United States Patent
Reay-Young et al.

[11] Patent Number: 6,080,154
[45] Date of Patent: Jun. 27, 2000

[54] LOCATING ANCHOR

[75] Inventors: Clive Bruce Reay-Young; Nicholas Paul Woods, both of Harrogate, United Kingdom; Björn Engström, Bromma, Sweden; Søren Winge, Roskilde, Denmark

[73] Assignee: Atlantech Medical Devices Limited, Harrogate, United Kingdom

[21] Appl. No.: 09/045,024

[22] Filed: Mar. 20, 1998

[30] Foreign Application Priority Data

Mar. 22, 1997 [GB] United Kingdom .................. 9705992

[51] Int. Cl.⁷ .................................................. A61B 17/56
[52] U.S. Cl. ............................................................ 606/60
[58] Field of Search .................................... 606/151, 172, 606/75, 232, 53, 218, 219, 220, 217, 233, 69, 142

[56] References Cited

U.S. PATENT DOCUMENTS

| | | | |
|---|---|---|---|
| 3,896,500 | 7/1975 | Rambert et al. ................................ | 3/1 |
| 5,147,361 | 9/1992 | Ojima et al. ............................... | 606/61 |
| 5,306,301 | 4/1994 | Graf et al. ................................. | 623/13 |
| 5,475,553 | 12/1995 | Baumgart .................................. | 606/71 |

FOREIGN PATENT DOCUMENTS

| | | |
|---|---|---|
| 296 07 352 U1 | 9/1996 | Germany . |
| 2 288 739 | 11/1995 | United Kingdom . |
| 2288739 | 1/1996 | United Kingdom ................... 606/232 |

*Primary Examiner*—Michael Buiz
*Assistant Examiner*—Tan-Uyen T. Ho
*Attorney, Agent, or Firm*—Nikaido, Marmelstein, Murray & Oram LLP

[57] ABSTRACT

A locating anchor for a replacement ligament is described. The anchor comprises a bar which is operable to extend across the opening of a bone tunnel through which the replacement ligament passes. The bar has a number of characterising features. The bar may not include any lateral support, the bar may be recessed, the bar may have a fixing groove, preferably, for ligament sutures or fixing means may be provided at each end of the bar to fix the ends of the bar in the bone surrounding the tunnel opening. A method of fixation is also defined. The bar is particularly useful in avoiding hindrance to the surgeon caused by the necessity to thread sutures through the fixation device.

21 Claims, 5 Drawing Sheets

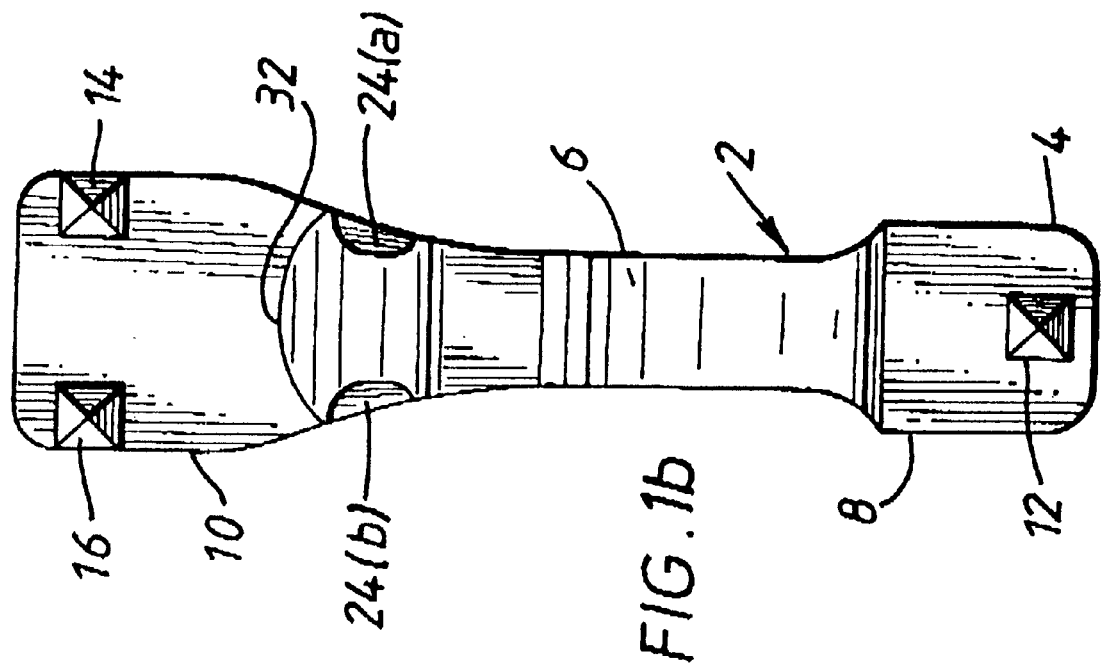
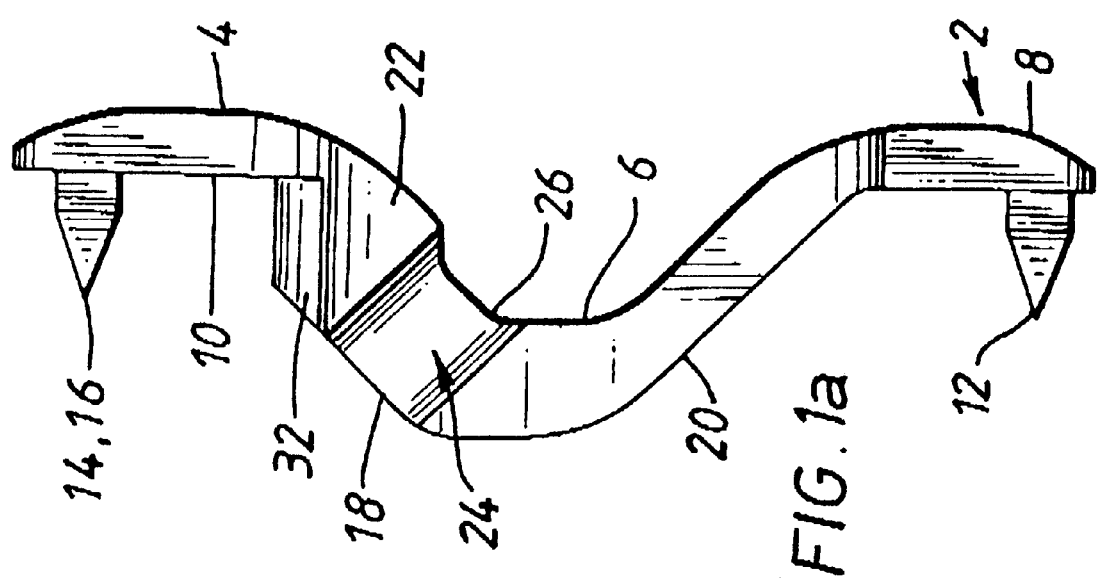

LOCATING ANCHOR

The present invention relates to a locating anchor for a replacement ligament.

Ligament damage and subsequent replacement is becoming an increasingly important issue facing modern surgeons. Modern sport and leisure activities are becoming an increasingly important aspect of daily life and modern sports demand an increasing level of fitness from its participants. Forces applied to knee ligaments, particularly the Anterior Cruciate (ACL) and Posterior Cruciate (PCL) ligaments, and particularly in active sports result in a high and increasing incidence of ligament injuries.

A number of techniques have been made available to replace damaged ligaments. One technique involves the removal of a graft comprising existing bone-tendon-bone, for example, a dissected section comprising the middle third of patellar tendon and the part of the bony insertion at each end of this tendon which is then used to replace the damaged ligament. The method of replacement involves the drilling of a tunnel, in the case of an ACL ligament, in each of the femur and the tibia into which the bone blocks are fixed, the tendinous part of the graft forming the replacement ligament across the inside of the knee joint.

Commonly the fixation of the bone blocks in the two tunnels is achieved by use of Titanium Screws which pass alongside the bone blocks, thereby producing an "Interference" fit.

The use of the Bone-tendon-bone with interference screw fixation is the most commonly employed method of ACL reconstruction. Unfortunately the technique has some disadvantages, namely post-operative problems associated with the donor site and secondly an increasing dislike in the surgical community of significant amounts of metal placed within or around the joint space.

In an attempt to address these issues an alternative type of graft is now in increasingly common use. The technique involves the harvesting and reimplantation of Semitendinosus and/or Gracilis tendons, known as "Hamstrings" or "Soft Tissue" grafts. The implantation technique is fundamentally the same except that there are no bone blocks with which to perform "interference screw" fixation. Fixation can be achieved in several ways, whether this be external to the joint or internal. Proximal (ie Femoral) fixation can be achieved by for example the use of a button/bar placed on the femoral cortex and connected to a loop of Graft using sutures or tapes through a tunnel in the femur. Alternatively, a Corin or Neoligament device may be used (for either femoral or tibial fixation) which both have recessed portions extending into the bone tunnel around which the loop of the replacement ligament may be passed. Both types of device are used for tensioning and are too deep seated for sutures to be tied thereon. Once femoral anchorage has been achieved there remains the problem of distal (ie Tibial) fixation. The problem here is to achieve fixation while the graft is held under some tension. Commonly fixation is achieved by means of a screw being placed in the anterior of the tibia and used as a post around which to tie sutures or otherwise secure the graft. In most circumstances a washer is placed under the head of the screw in order to achieve secure downward fixation. Unfortunately the technique has disadvantages: firstly the placement of a screw in the anterior tibia means that fixation is some way distant to the ultimate anchorage point of the graft in the tunnel. This means that either the span must be achieved with sutures or the graft must be long enough to reach across the joint, through the tibial tunnel, out of its opening and some way down the tibia to the fixation point. This is considered by some surgeons to be a waste of "good graft", these surgeons preferring to double or quadruple the graft and find a way of fixating this shorter but more substantial and therefore preferable graft in the tunnel. The second disadvantage is that the screw placed in the anterior tibia is often palpable and therefore uncomfortable for the patient post-operatively as the screw head sits on top of the tibial cortex.

A technique has been developed whereby the sutures fixed to the ends of the replacement ligament (graft) are tied to an anchor, located at the entrance to the tunnel. The anchor need not be screwed into position and is, therefore, simpler to position than the screw technique. The anchor comes in the form of a generally circular ring with a bar extending across the diameter of the ring to which the sutures are tied. The ring is designed to sit on the bone immediately bordering the almost circular entrance to the tunnel. Unfortunately, the technique necessitates the threading of sutures on either side of the bar between the bar and the inner circumference of the ring. This is a rather awkward task to perform during, for instance, key-hole surgery. Furthermore, in most instances, the tunnel is not perpendicular to the surface of the bone through which it passes and this tends to cause the sutures to "ride" along the bar in a direction in accordance with the angle of the tunnel. Furthermore, the anchor is fixed in position by the tension from the sutures and, therefore, is loose during tying, an inconvenience in the operative environment. Also, the bar is only slightly recessed, resulting in any knot remaining above the bone surface, again being palpable by the patient.

It is an object of the present invention to overcome the above problems together with other problems which will become apparent hereafter.

According to a first aspect of the present invention there is provided a locating anchor for a replacement ligament comprising a bar which is operable to extend across the opening of a bone tunnel through which the replacement ligament passes characterised in that the bar does not include any lateral support.

The replacement ligament or graft is usually a graft of bone tendon bone or soft tissue but may include suitable artificial replacements. It is not necessarily the original ligament or a ligament from another joint.

Preferably, fixing means are provided at each end of the bar to fix the ends of the bar in the bone surrounding the tunnel opening.

Preferably, the fixing means are pins. Typically, the pins depend downwardly from each end of the bar.

Preferably, the mid portion of the bar is recessed with respect to its ends so that it may be seated within the end of the tunnel. Preferably all the mid portion is seated within the tunnel.

Preferably, a locating groove is formed in the bar on its mid portion to locate the replacement ligament in use and thereby to prevent slippage.

The groove may extend only along the upper surface of the bar but, preferably, extends around the sides thereof to enhance the locating of the replacement ligament.

Tape/sutures attached to the replacement ligament may be tensioned and then tied around the groove so that the knot will sit in the recess and therefore will not protrude out of the entrance to the tunnel rendering the anchoring device more comfortable for the patient.

Where the tunnel is angled with respect to the surface of the bone where the opening to the tunnel is found, the locating anchor may be recessed in such a way that the angle of the recessing portion of the bar extending from one end to the recessed mid portion is approximately equal to the angle between the surface of the bone and the tunnel so that the recessed portion is easily located in the tunnel. Furthermore, the base of the recess is, preferably, formed to be substantially perpendicular to the tunnel which assists in preventing movement of the sutures after fixation and transmitting force from sutures through the device in the most anatomic fashion.

The replacement ligament may be made of any suitable material available to the skilled man. It may be an homograft (same patient), allograft (different person) or consist of suitable artificial or other materials.

Preferably, the end of each strand of replacement ligament is stitched with at least one suture for tying the ligament to the anchor.

Typically, the locating device is used in anterior cruciate ligament (ACL) fixation. A typical application would be as a replacement to the currently used screw on the tibia ie as a tibia locating anchor for ACL fixation. The device may also be used in PCL fixation or other replacement ligament fixation where a bone tunnel is required.

The bar may be made of any of the suitable materials known to the skilled man. Preferably, however, it is made from Titanium Alloy 6A1 4V ELI. Preferably, the bar is longitudinal as seen from above.

A second aspect of the present invention is a method of anchoring a replacement ligament comprising the steps of:

tying at least one end of the replacement ligament to a locating anchor comprising a bar which extends across the opening of a bone tunnel through which the replacement ligament passes characterised in that the bar does not include any lateral support.

The said method, preferably, includes any one or more of the following steps:

forming a tunnel in the bone to which the ligament is to be anchored;

threading the replacement ligaments through the said tunnel;

fixing a locating anchor in accordance with the first aspect of the present invention at the entrance to the tunnel;

tying the replacement ligament to the locating bar which is fixed at the end of the tunnel;

tying the other end to a further locating anchor in accordance with the first aspect of the invention.

Advantageously, the absence of any lateral support which was seen as being necessary to provide lateral stability to the anchor provides a considerable advantage in that it is no longer necessary to thread the sutures, located at each end of the replacement ligament, through the locating anchor. This considerably eases the surgical technique. The sutures protruding through the opening of the tunnel can simply be parted so that the anchor can be placed between them. No threading is necessary.

According to a third aspect of the present invention there is provided a locating anchor for a replacement ligament comprising a bar which is operable to extend across the opening of a bone tunnel through which the replacement ligament passes, the mid portion of the bar being recessed with respect to its ends so that it may be seated within the end of the tunnel to an extent which allows a knot to be tied thereto and to be wholly contained within the tunnel, characterised in that fixing means are provided to fix the anchor to the bone prior to tying of the knot.

Preferably, the anchor is recessed in such a way that the angle of the recessing portion of the bar extending from one end to the recessed midportion is approximately equal to the angle between the surface of the bone and the tunnel so that the recessed portion is easily located in the tunnel and the anchor ends may abut against the bone surface.

Preferably, the recessed portion is substantially perpendicular to the axis of the tunnel.

Advantageously, the invention in accordance with the third aspect of the present invention, allows the surgeon to tie a knot with the sutures which may be wholly located within the recess.

According to a fourth aspect of the present invention there is provided a locating anchor in accordance with the pre characterising part of the first aspect of the present invention characterised in that a locating groove is formed in the bar on its mid portion to locate the replacement ligament, and thereby to prevent slippage in use. Advantageously, this creates an immobile fixation which is likely to encourage healing of the "graft" in the tunnel.

According to a fifth aspect of the present invention there is provided a locating anchor in accordance with the pre characterising portion of the first aspect of the present invention characterised in that fixing means are provided at each end of the bar to fixedly secure the ends of the bar to the bone around the tunnel opening.

Preferably, the fixing means are pins, typically, the pins project downwardly from each end of the bar.

The use of the fixing means, prevents the bar laterally twisting, in use, and also provides a major advantage by holding the bar in place during the surgical tensioning and fixation of the replacement ligament.

For the avoidance of doubt, any of the features defined with reference to the first to fifth aspects of the present invention which includes the post characterising feature itself and each of the optional features either with or without the post-characterising feature may be combined with any of the other aspects except where any such combinations are mutually exclusive.

The present invention has applications for use with bone-tendon-bone graft as well as soft tissues. In ACL grafts it could be considered for fixation at either the femoral or tibial ends of the graft, although tibial is preferred.

An embodiment of the invention will now be described, by way of example, with reference to the accompanying drawings in which:

FIG. 1a shows a side view of a locating anchor in accordance with the present invention;

FIG. 1b shows an underplan view of a locating anchor in accordance with the present invention;

Figure 2:
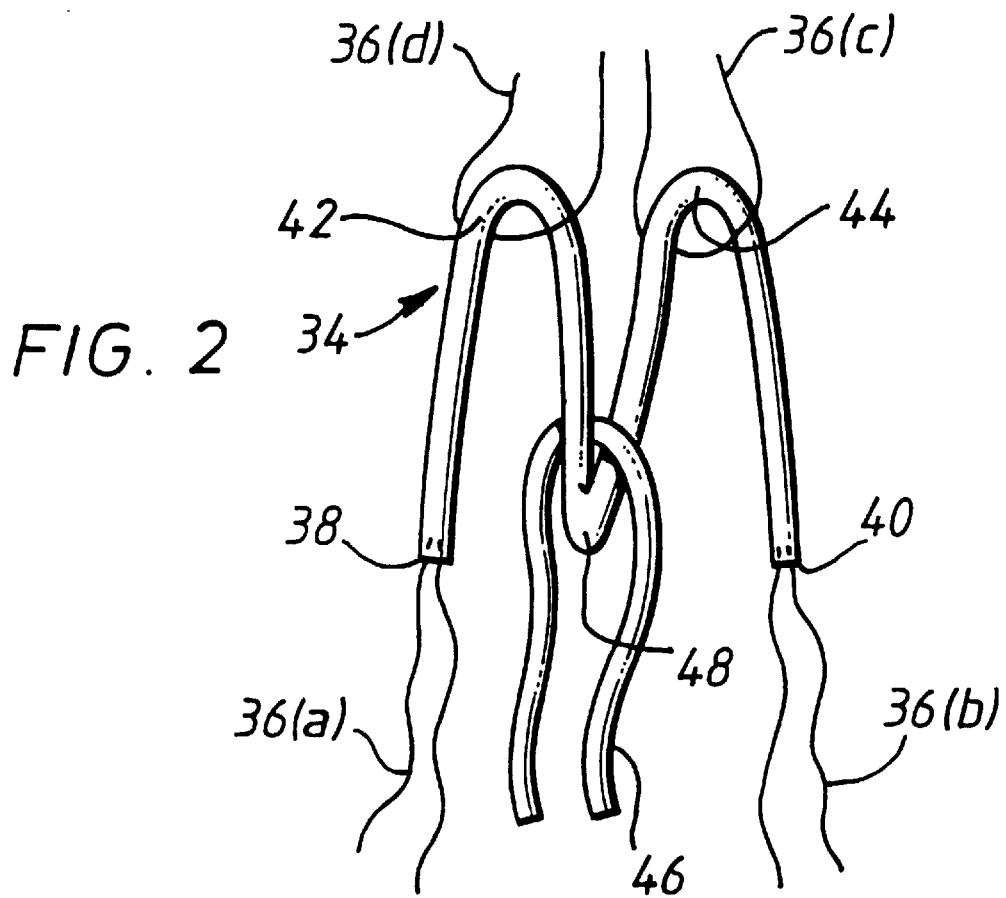
FIG. 2 shows a schematic representation of the replacement ligament.
Figure 3:
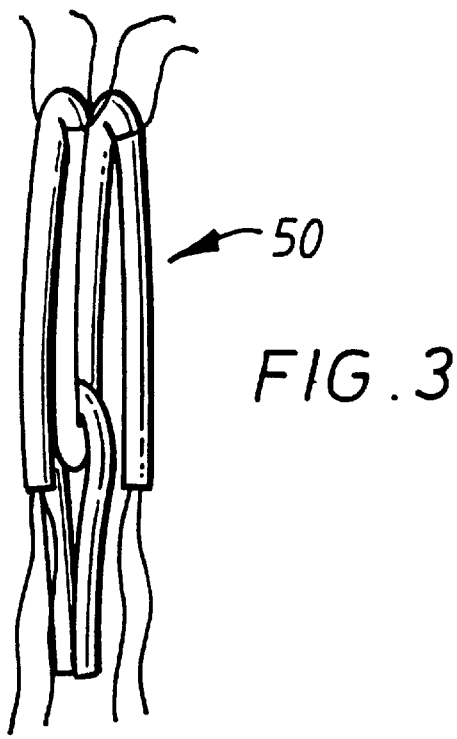
FIG. 3 shows the replacement ligament prior to fixation.

Referring to FIGS. 1a and 1b, a fixation device for a replacement ligament is in the form of a locating anchor 2 which comprises a longitudinal bar 4 which is recessed in its mid portion 6 between two coplanar and aligned ends 8,10 and recessing arms 20, 22. Three locating pins 12,14 and 16 depend downwardly from the underside of the ends, two (14, 16) being located at either side of the wider upper end (10) and the third (12) being centrally located in the lower end (4). The upper end 10 being subject to greater forces than the lower end 4 is wider so as to provide greater stability to the anchoring device in use. The recessed portion 6 is located downwardly and angularly with respect to the underside of the ends 8,10 so that the base 18 of the recess is located at an angle to the plane of the ends 8,10. Accordingly, the first arm recession 20 of the recess is longer than the second recessing arm 22 to provide for the angular displacement of the base of the recess from the plane of the ends.

As a result of this construction, the recessed mid-portion can be designed to be substantially perpendicular to the axis of the bone tunnel in which it is to be located. The replacement ligament may thus be located so that it is secured around the recessed portion of the locating anchor which allows the force acting along the ligament to act at right angles to the recess and thus prevent any movement of the fixed ligament along the length of the recess bar.

A locating groove 24 is located on either side of the recess extending at right angles thereto from the base 18 of the recess to its upper surface 26. The upper surface 26 is itself rounded along the longitudinal axis of the bar in that the recessions arms 20,22 do not meet in an angular fashion. The location of the rounded junction of the two arms is located above the grooves 24a, 24b so that a three sided groove is effectively formed around the recessed portion of the locating anchor. The three sided groove provides a convenient means in which to locate and tension the sutures 36 of the graft and, thereafter, to encourage the ligament to remain in place. As the tension of the ligament acting on the locating anchor can be resolved into two forces, one acting to drive the locating anchor into the bone face and the second action to drive the locating anchor in a direction from the long recessing arm towards the short recessing arm, the reverse side 32 of the short arm is rounded to remove any cutting edges. The pins 12, 14 and 16 are square in section to assist fixation of the locating anchor.

Referring to FIG. 2, a schematic view of a typical replacement ligament assembly is shown. In this embodiment, the ligament is entirely made from soft tissue and comprises an approximately "M" shaped ligament graft 34 having sutures 36 at each of its ends 38, 40 and two polyester tapes through its upper arches 42,44. Additionally, a further tape 46 is threaded around the lower arch 48 of the "M". In use, the ligament is tensioned so that the parts are pulled together to form a bundle of bands 50 with the tape and sutures extending from either end thereof.

Figure 4:
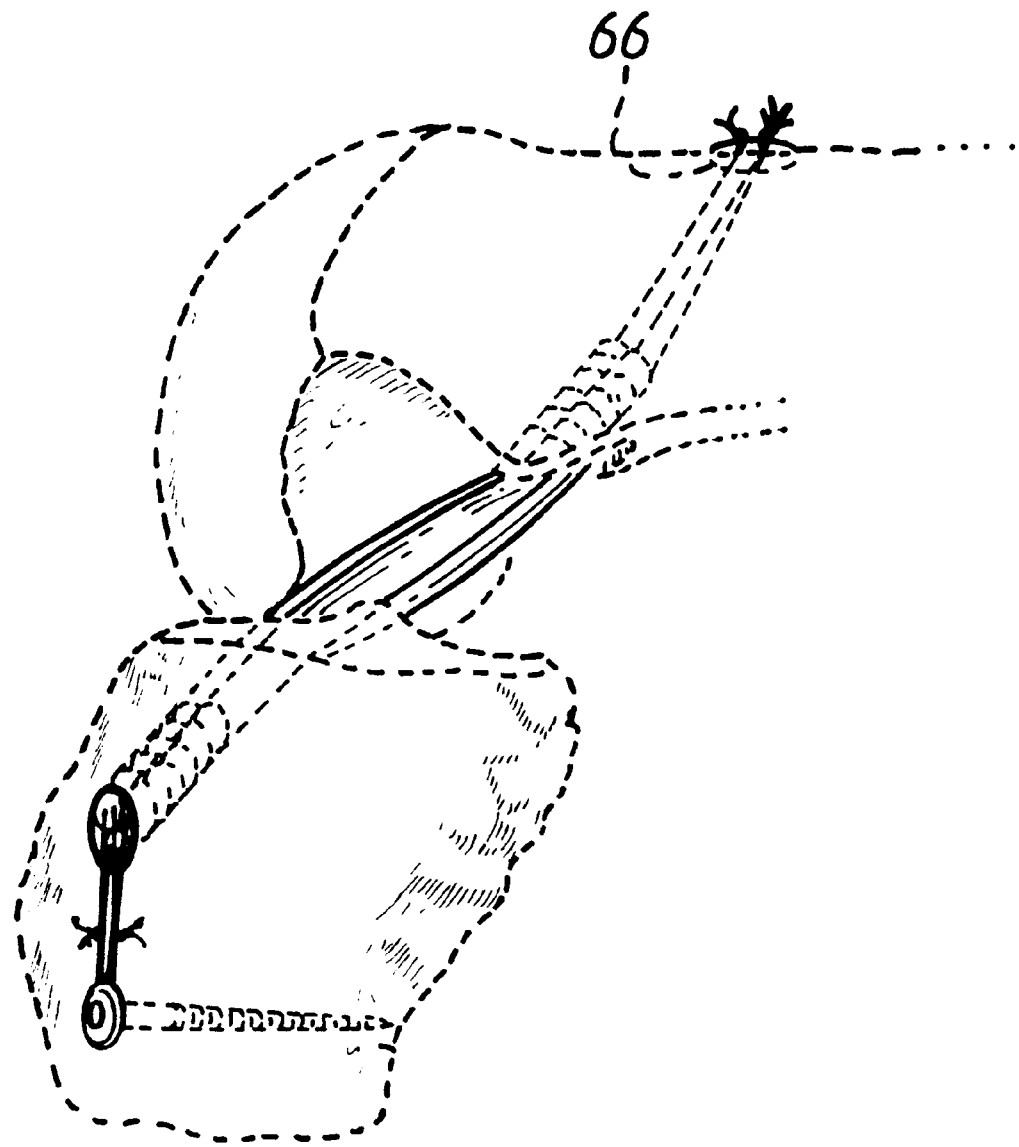
FIG. 4 shows a lateral view of the location of a replacement ligament using the prior art fixation anchors.
Figure 5:
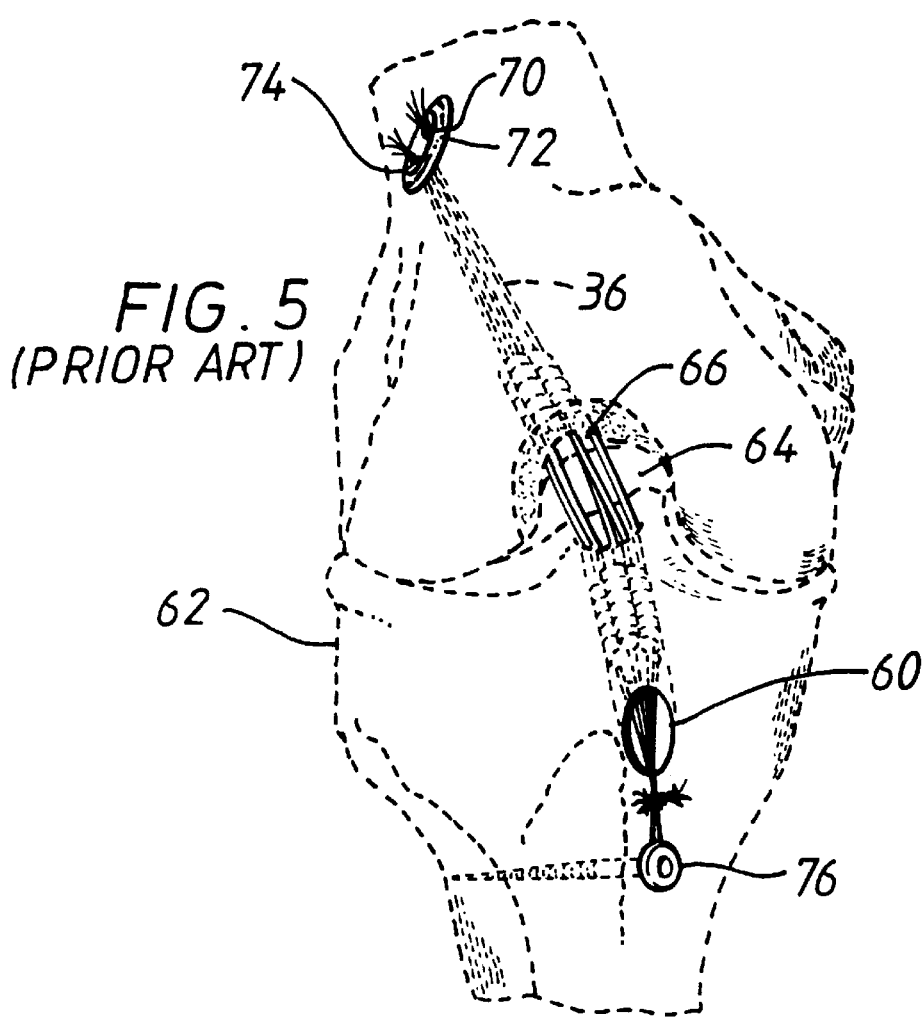
FIG. 5 shows a front view of the prior art arrangement of FIG. 4.
Figure 6:
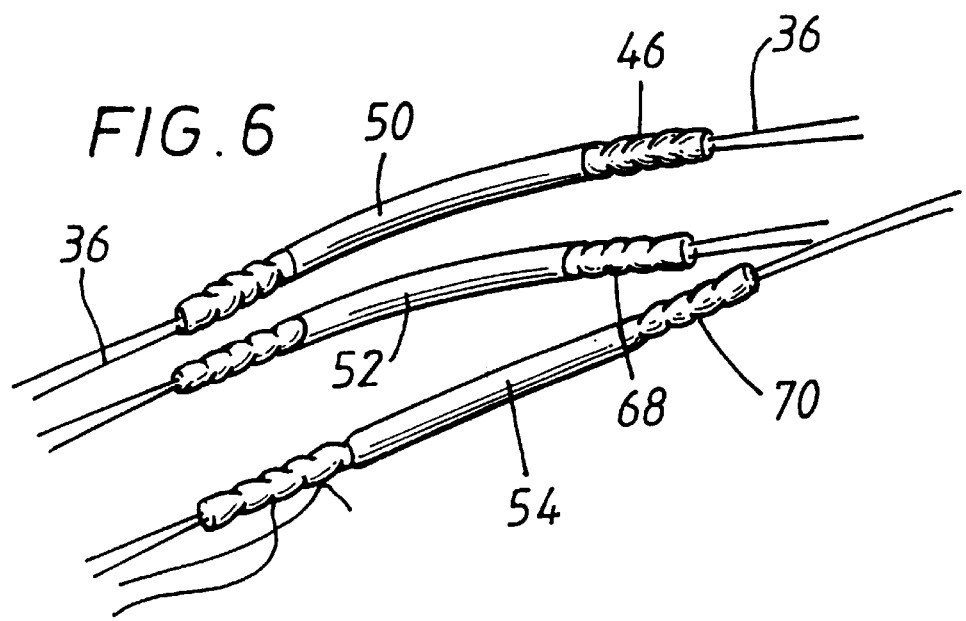
FIG. 6 shows three replacement ligaments prior to fixation.

Referring to FIGS. 4 and 5, the two prior art arrangements for locating the ends of the replacement ligament are clearly shown. A hole 60 is drilled through the front of the tibia 62 to pass posteriorly and superiorly to emerge in the condylar cavity 64. A second hole 66 is drilled through the femur from the condylar cavity to pass superiorly and anteriorly with respect to the joint in extension. Such an arrangement allows the bundle of ligaments to mimic the positioning of the anterior cruciate ligament. As can be seen from FIG. 6, each replacement ligament contains a bundle of ligaments 50, 52 and 54 which are taped at either end thereof and which have sutures extending beyond each end for fixation purposes.

Referring again to FIGS. 4 and 5, the upper sutures are secured in the femur by being tied around a fixation button 70 of which several types will be known to the skilled man. A fixation post is provided in the tibia by means of a threaded screw 76 which is secured in the front of the tibia at right angles to the axis of the bone and approximately 1" below the entrance to the tibial bone tunnel. The sutures may thereafter be passed around the fixation post provided by the shank of the screw, tensioned and tied in position. It is important that the ligament is correctly tensioned around the fixation post after the femoral fixation has taken place. The correct tensioning can only be achieved, under surgical conditions, by having the tibial fixation device fixed in position prior to tensioning.

Figure 7:
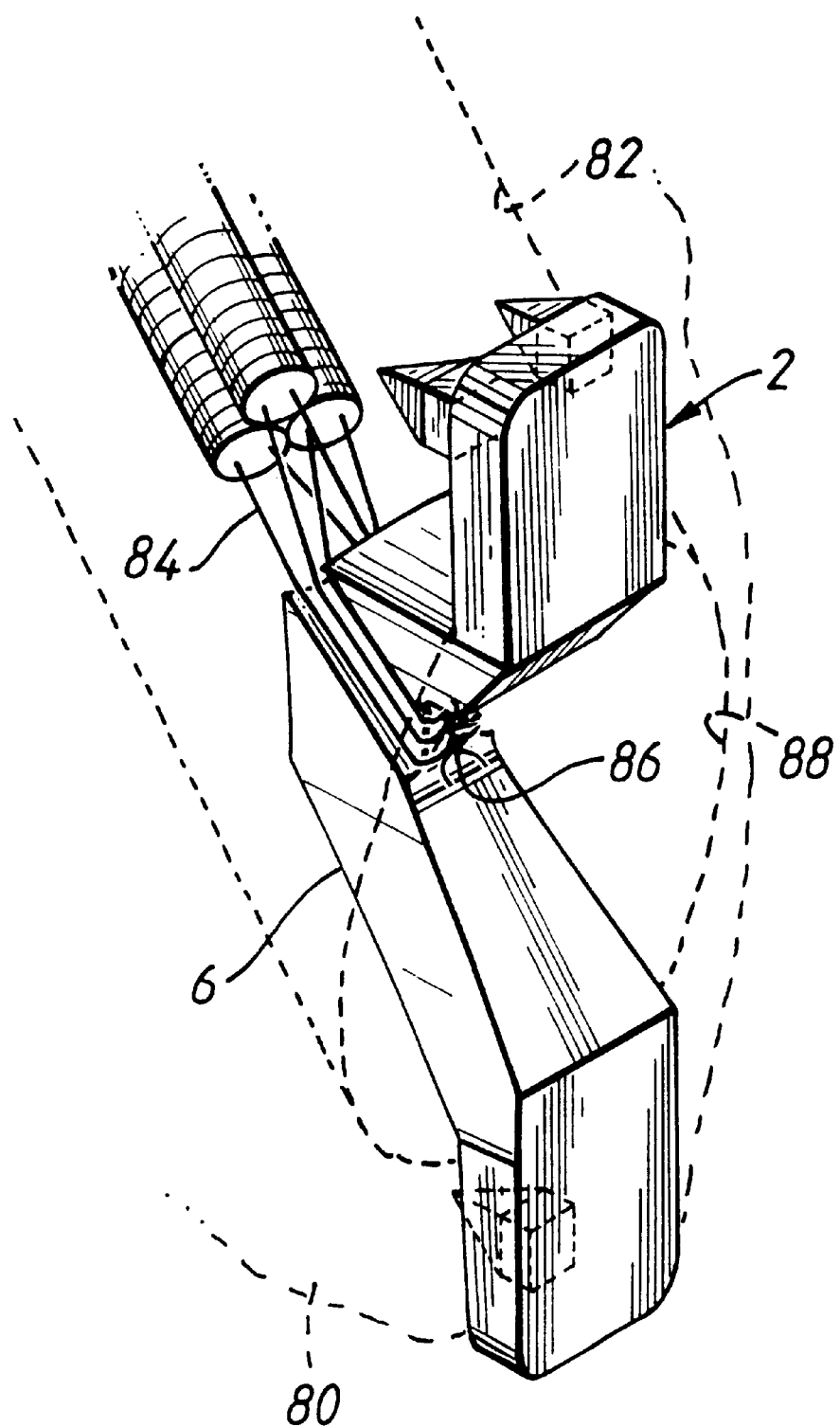
FIG. 7 shows a partial view of the locating anchor and ligament after fixation.

Referring to FIG. 7, the locating device 2 is shown secured to the face of the tibia 80 so that the recessing arms 20, 20 extend into the bone tunnel 82 in a posterior and superior direction. The sutures 84 are secured around the locating grooves 24, 26 and firmly secured so that the knots 86 do not protrude above the surface of the bone face through the hole 88. The fixing pins hold the locating bar in position while the sutures 84 are correctly tensioned. Furthermore, the underside of the ends 8, 10 firmly butt against the surface of the tibia to prevent any lateral movement in the locating anchor rendering it unnecessary to utilise a ring. The lateral support is further assisted by the twin pins protruding into the tibia from either side of the superior end of the locating device.

It should be noted that although the above example refers to ACL fixation, this invention is not limited to this application and it will be clear to the skilled man that it has numerous applications in connection with the replacement of ligaments involving the drilling of bone tunnels.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

We claim:

1. A locating anchor for a replacement ligament comprising:
   a bar sized to extend vertically across an opening of a bone tunnel through which the replacement ligament passes wherein the bar is connectable to the replacement ligament and has a width smaller than a width of the opening of the bone tunnel such that the bar does not include any lateral support.

2. A locating anchor for a replacement ligament as claimed in claim 1, wherein fixing means are provided at each end of the bar to fix the ends of the bar in a bone surrounding the tunnel opening.

3. A locating anchor for a replacement ligament as claimed in claim 2, wherein the fixing means are pins.

4. A locating anchor for a replacement ligament as claimed in claim 3, wherein the pins depend downwardly from each end of the bar.

5. A locating anchor for a replacement ligament as claimed in claim 1, wherein the bar further comprises a mid portion, the mid portion of the bar is recessed with respect to ends of the bar so that the bar is seatable within an end of the bone tunnel.

6. A locating anchor for a replacement ligament as claimed in claim 5, wherein all of all the mid portion is seated within the bone tunnel.

7. A locating anchor for a replacement ligament as claimed in claim 5, further comprising a locating groove formed in the mid portion of the bar to locate the ligament in use and thereby to prevent slippage of the ligament.

8. A locating anchor for a replacement ligament as claimed in claim 7, wherein the location the groove extends only along an upper surface of the bar.

9. A locating anchor for a replacement ligament as claimed in claim 7, wherein the locating groove extends around sides of the bar to enhance the locating of the ligament.

10. A locating anchor for a replacement ligament as claimed in claim 1, wherein the locating anchor is recessed such that an angle of a recessed portion of the bar extends from one end of the to the recessed mid portion and is substantially equal to an angle between a surface of the bone and the bone tunnel.

11. A locating anchor for a replacement ligament as claimed in claim 5, wherein a base of the recessed mid portion is substantially perpendicular to an axis of the bone tunnel.

12. A locating anchor for a replacement ligament as claimed in claim 1, wherein the locating anchor is one of either an anterior cruciate ligament and a posterior cruciate ligament fixation device.

13. A method of anchoring a replacement ligament comprising the following steps:

placing a locating anchor within a bone tunnel such that a bar of the locating anchor extends vertically across an opening of the bone tunnel through which the replacement ligament passes wherein the bar is connectable to the replacement ligament and has a width smaller than a width of the opening of the bone tunnel such that the bar does not include any lateral support; and tying at least one end of the replacement ligament to the locating anchor.

14. A method of anchoring a ligament as claimed in claim 13, further comprising an additional step of forming the bone tunnel in a bone to which the ligament is to be anchored before the placing step.

15. A method of anchoring a ligament as claimed in claim 13, further comprising an additional step of threading the ligament through the bone tunnel.

16. A method of anchoring a ligament as claimed in claim 13, further comprising an additional step of fixing the locating anchor at an entrance of the bone tunnel.

17. A method of anchoring a ligament as claimed in claim 16, further comprising an additional step of tieing the ligament over the bar fixed at an end of the bone tunnel.

18. A locating anchor for a replacement ligament comprising:

a bar sized to extend vertically across an opening of a bone tunnel through which the replacement ligaments passes wherein the bar is connectable to the replacement ligament and has a width smaller than a width of the opening of the bone tunnel such that the bar does not include any lateral support, a mid portion of the bar is recessed with respect to ends of the bar and is seated within an end of the bone tunnel to allow a knot to be tied to the recessed mid portion and to be wholly contained within the bone tunnel; and fixing means to fix the locating anchor to the bone prior to tying the knot to the recessed mid portion.

19. A locating anchor for a replacement ligament comprising:

a bar sized to extend vertically across an opening of a bone tunnel through which the replacement ligament passes and the bar is connectable to the replacement ligament; and a locating groove is formed on a mid portion of the bar to locate the ligament and prevent the ligament from slipping along the bar, wherein a width of the bar is smaller than a width of the opening of the bone tunnel such that the bar does not include any lateral support.

20. A locating anchor for a replacement ligament comprising:

a bar sized to extend vertically across an opening of a bone tunnel through which the replacement ligament passes and the bar is connectable to the replacement ligament; and fixing means at each end of the bar to fixedly secure the ends of the bar in a bone surrounding the bone tunnel opening, wherein a width of the bar is smaller than a width of the opening of the bone tunnel such that the bar does not include any lateral support.

21. A locating anchor according to claim 1, wherein the bar is configured to have the replacement ligament tied to the bar.

* * * * *